United States Patent
Audouin

(10) Patent No.: US 9,243,945 B2
(45) Date of Patent: Jan. 26, 2016

(54) DEVICE FOR MEASURING A QUANTITY OF A REDUCING AGENT, PREFERABLY NH3, CONTAINED IN A VESSEL

(75) Inventor: Arnaud Audouin, Paris (FR)

(73) Assignee: AAQIUS & AAQIUS SA, Geneva (CH)

( * ) Notice: Subject to any disclaimer, the term of this patent is extended or adjusted under 35 U.S.C. 154(b) by 34 days.

(21) Appl. No.: 14/117,360

(22) PCT Filed: May 14, 2012

(86) PCT No.: PCT/EP2012/058936
§ 371 (c)(1),
(2), (4) Date: Apr. 17, 2014

(87) PCT Pub. No.: WO2012/156371
PCT Pub. Date: Nov. 22, 2012

(65) Prior Publication Data
US 2014/0216010 A1 Aug. 7, 2014

(30) Foreign Application Priority Data
May 13, 2011 (EP) .................................... 11003978

(51) Int. Cl.
*F01N 3/00* (2006.01)
*G01F 22/02* (2006.01)
*F01N 3/20* (2006.01)
*F17C 11/00* (2006.01)

(52) U.S. Cl.
CPC .............. *G01F 22/02* (2013.01); *F01N 3/208* (2013.01); *F01N 3/2066* (2013.01); *F17C 11/00* (2013.01); *F01N 2610/02* (2013.01); *F01N 2610/06* (2013.01); *F01N 2610/1406* (2013.01); *F01N 2900/102* (2013.01); *F01N 2900/1808* (2013.01); *F01N 2900/1814* (2013.01); *Y02E 60/321* (2013.01); *Y02T 10/24* (2013.01)

(58) Field of Classification Search
USPC .......................... 60/286, 295, 297, 301, 303
See application file for complete search history.

(56) References Cited

U.S. PATENT DOCUMENTS

| | | | |
|---|---|---|---|
| 4,600,525 A | 7/1986 | Baker et al. | |
| 6,550,250 B2* | 4/2003 | Mikkelsen et al. | 60/685 |
| 7,393,187 B2* | 7/2008 | Weigl | 417/413.1 |
| 7,966,811 B2* | 6/2011 | Reed | 60/286 |
| 8,679,209 B2* | 3/2014 | Korenev | 55/282.3 |
| 8,943,808 B2* | 2/2015 | Li et al. | 60/295 |
| 2006/0184307 A1 | 8/2006 | Kosaka | |
| 2010/0154907 A1* | 6/2010 | Lecea et al. | 137/565.29 |

FOREIGN PATENT DOCUMENTS

| | | |
|---|---|---|
| DE | 10 2009 022884 A1 | 12/2012 |
| EP | 1 977 817 A1 | 10/2008 |
| WO | WO 2006012903 A2 | 2/2006 |

\* cited by examiner

*Primary Examiner* — Binh Q Tran
(74) *Attorney, Agent, or Firm* — Blakely Sokoloff Taylor & Zafman LLP

(57) ABSTRACT

The invention relates to a device for measuring a quantity of a reducing agent, preferably NH₃, contained in a vessel (10; 110; 210) containing a storage material (11; 111; 211) in which the reducing agent is stored, the volume of the storage material (11; 111; 211) varying depending on the quantity of reducing agent which it contains. The measuring device comprises means (13, 14, 14'; 113, 114; 213, 214) associated with the vessel (10; 110; 210), said means being suitable for measuring the quantity of reducing agent stored in the storage material (11; 111; 211) depending on the volume of the latter.

22 Claims, 4 Drawing Sheets

① Salt + Additive powder

② Salt + Additive compacted

③ Salt + Additive loaded with NH3     ④ Salt + Additive emptied of NH3

DEVICE FOR MEASURING A QUANTITY OF A REDUCING AGENT, PREFERABLY NH3, CONTAINED IN A VESSEL

The proposed invention relates to a device for measuring the level of a reducing agent contained in a vessel. The invention also relates to a method for controlling the injection of the reducing agent into the exhaust gases of a motor vehicle.

Transport-related pollutant emissions have for nearly thirty years been at the forefront for prompting progress in the industry. Increasingly more stringent emission limits for the four regulated pollutants (CO, HC, NOx, particles) have allowed a significant improvement in air quality, in particular in large cities The ever increasing use of motor vehicles requires continued efforts to further reduce these pollutant emissions. Therefore, the reduction of nitrogen oxides (NOx) remains a complex problem within the context of more stringent European thresholds expected in 2015 when the Euro 6 standard comes into force. To have available highly efficient depolluting technologies under all driving conditions remains a major challenge for the transport industry.

Secondly, fuel consumption directly linked with $CO_2$ emissions has become a major concern. For example, regulations will be introduced at European level beginning in 2012 relating to passenger vehicle $CO_2$ emissions. It is henceforth accepted that this limit will be regularly lowered over the coming decades. $CO_2$ reduction has therefore become an obvious necessity for the entire transport industry.

This dual issue of reducing local pollution (NOx) and reducing fuel consumption ($CO_2$) raises particularly difficulties for diesel engines whose lean-burn combustion is accompanied by NOx emissions that are difficult to treat.

Devices already exist, such as that disclosed in EP1977817, which allow a reduction in NOx quantities by means of a selective catalytic reduction (SCR) catalyzer via ammonia stored in a storage material of the alkaline-earth chloride salt type arranged inside a vessel. The injection of ammonia into exhaust gases is controlled by means of a heating device used to heat the storage material to allow a reversible absorption/desorption reaction of ammonia, since this reaction is directly related to the temperature within the storage material.

In practice, ammonia is injected into the exhaust continuously in stoichiometric proportions of the NOx reduction reaction. It is thus advisable to be able to store on-board a sufficient quantity of ammonia. To limit the size of the vessel containing the storage material, automobile manufacturers favor filling or replacing the vessel periodically, for example during engine maintenance (oil change) or when refueling. Depending on the vehicles (passenger vehicles, heavy trucks, etc.), it is necessary to expect between 10 and 100 vessel filling or vessel replacement operations over the vehicle's lifespan.

This periodic maintenance service, needed to ensure effective depollution of NOx throughout the life of the vehicle, is the object of specific regulations in the various countries where SCR technology is used. A point common to all these regulations is the need to be able to determine the quantity of ammonia remaining in the vessel so as to be able to inform the driver when refueling is needed. For example, in European legislation for passenger vehicles, it is necessary to be able to measure at least two thresholds of remaining range, at 2400 km and 800 km (corresponding to about 3 fill-ups and 1 fill-up of fuel, respectively).

Furthermore, if several vessels each comprising an ammonia storage material are on-board the vehicle so as to simplify integration of the ammonia storage system in the vehicle, or to improve its operation (introduction of a cooling unit), it is necessary to know the quantity of ammonia remaining in each vessel so that the engine computer can optimally control the injection of ammonia contained in these various vessels.

The document DE 10 2009 022884 A1 discloses for its part a device for measuring the quantity of ammonia on the basis of the variation of capacitance of a capacitor.

The document US 2006/184307 A1 discloses a method for controlling the injection of a reducing agent by comparing average consumption and a threshold value so as to, if need be, limit this consumption.

An objective of the present invention is to propose a device for measuring the level of a reducing agent, preferably ammonia, contained in a vessel.

According to the invention, this objective is achieved by means of a device for measuring a quantity of a reducing agent, preferably $NH_3$, contained in a vessel containing a crystal lattice (hereafter storage material) in which the reducing agent is stored, the volume of the storage material varying depending on the quantity of reducing agent which it contains. The measuring device comprises means associated with the vessel, said means being suitable for measuring the quantity of reducing agent stored in the storage material depending on the volume of the latter. Said means are arranged on the one hand for measuring mechanical stress generated by expansion of the storage material, and on the other hand for converting the stress measurement into a quantity of reducing agent stored in the storage material.

Another aspect of the invention relates to a method for controlling the injection of a reducing agent into the exhaust gases of a motor vehicle, comprising at least the following steps:

measuring the quantity of reducing agent in a vessel feeding the engine with the measuring device as defined above, determining the average consumption of reducing agent since the last vessel maintenance service, comparing said average consumption with at least one threshold value in order to, if need be, limit this consumption so as to have a sufficient quantity of reducing agent to reach the theoretical step of the next vessel maintenance service.

The characteristics of the invention will become more clearly apparent on reading the description of several variations of embodiments, given solely as examples which are in no way limiting, with reference to the drawings in which.

The various embodiments according to the invention which are disclosed below rest on the fact that during the absorption reaction, the fixing of ammonia in a salt of the metal chloride type is accompanied by an increase in volume, the ammoniate then occupying a much greater volume than the volume of the pure salt (up to a ratio of 4 to 5 times). The increase in the volume of the salt is due not only to expansion of its crystal lattice but also to its fractionation, thus leaving free space between the microcrystals of the ammoniate complex.

Figure 1:
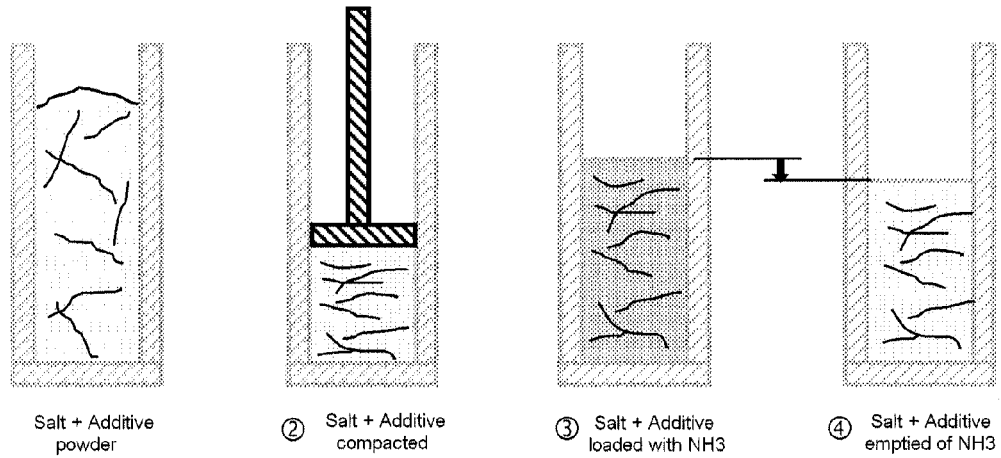
FIG. 1 represents the essential steps of the preparation of the storage material.

According to the invention, the storage material preferably comprises expanded natural graphite so that this material has better thermal conductivity on the one hand and is more robust on the other. According to the preparation of this storage material as illustrated by FIG. 1, expanded natural graphite is added to the salt before being compacted according to a unidirectional axis. In this way, the expansion that results from the saturation of the material with ammonia occurs first and foremost according to the compression axis and to a lesser extent perpendicular to the compression axis. Therefore, it is possible to control the expansion of the material according to the compression axis, the relevance being to limit the stress applied to the walls of the storage vessel.

Then, during desorption of ammonia, the network created by the recompressed expanded natural graphite forms a robust structure which maintains the salt particles emptied of ammonia. Depending on the quality of implementation, an expansion of between 1% and 10% according to the compression axis and on the order of 0.01% to 1% according to the axis perpendicular to the compression axis is observed.

Figure 2:
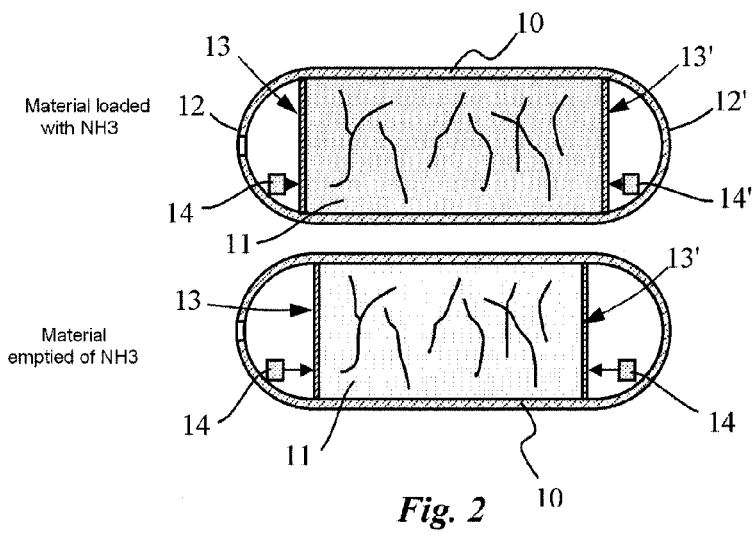
FIG. 2 illustrates the vessel comprising the storage material respectively loaded with and empty of ammonia according to a first configuration.

According to a first embodiment as illustrated in FIG. 2, the vessel 10 containing the storage material 11 has symmetry of revolution, preferentially cylindrical, this vessel 10 being closed at both ends by two hemispheres 12, 12'. A first and a second disc 13, 13' permeable to ammonia gas are arranged on both sides of the storage material 11 and are able to move according to the compression axis of said material 11. A first and a second piezoelectric sensor 14, 14' are positioned in one and the other of the hemispheres 12, 12', respectively, so as to be in contact with the first and second discs 13, 13', respectively, so as to measure the expansion of the storage material 11 according to its compression axis during desorption of ammonia.

Figure 3:
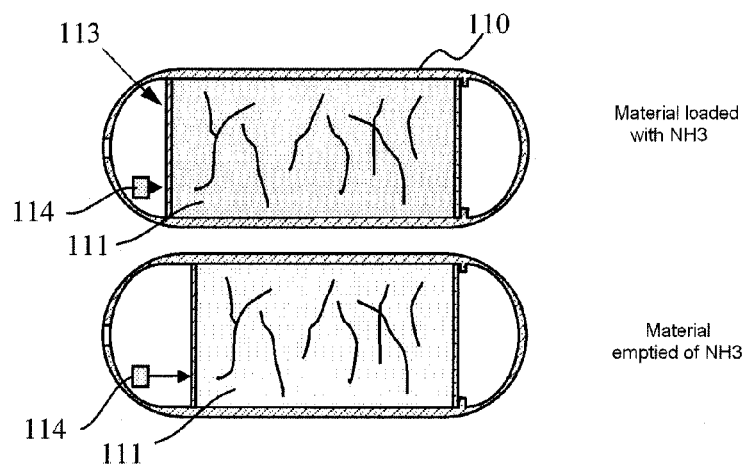
FIG. 3 illustrates the vessel comprising the storage material respectively loaded with and empty of ammonia according to a second configuration.

According to a second embodiment of the invention as illustrated in FIG. 3, a first and a second disc 113, 113' permeable to ammonia gas are arranged on both sides of the storage material 111 inside the vessel 110. The first disc 113 is able to move according to the compression axis of the material 111 whereas the second disc 113' is fixed. A piezoelectric sensor 114 is positioned so as to be in contact with the first disc 113 so as to be able to measure the expansion of the storage material 111 according to its compression axis during desorption of ammonia.

Figure 4:
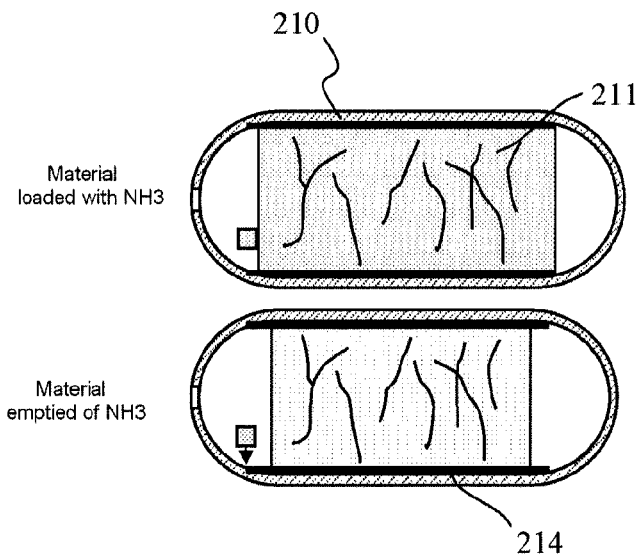
FIG. 4 illustrates the vessel comprising the storage material respectively loaded with and empty of ammonia according to a third configuration.

According to a third embodiment of the invention as illustrated in FIG. 4, expansion that occurs perpendicular to the compression axis of the storage material 211 is measured. In this case, a piezoelectric material 214 covering all the external surface of the storage material 211 is positioned between the vessel 210 and the storage material 211. As the storage material 211 is emptied of ammonia, the mechanical stress applied to the piezoelectric material 214 decreases.

Let us specify that any other means suitable for measuring expansion of the storage material can be used in place of one or more piezoelectric sensors.

Figure 5:
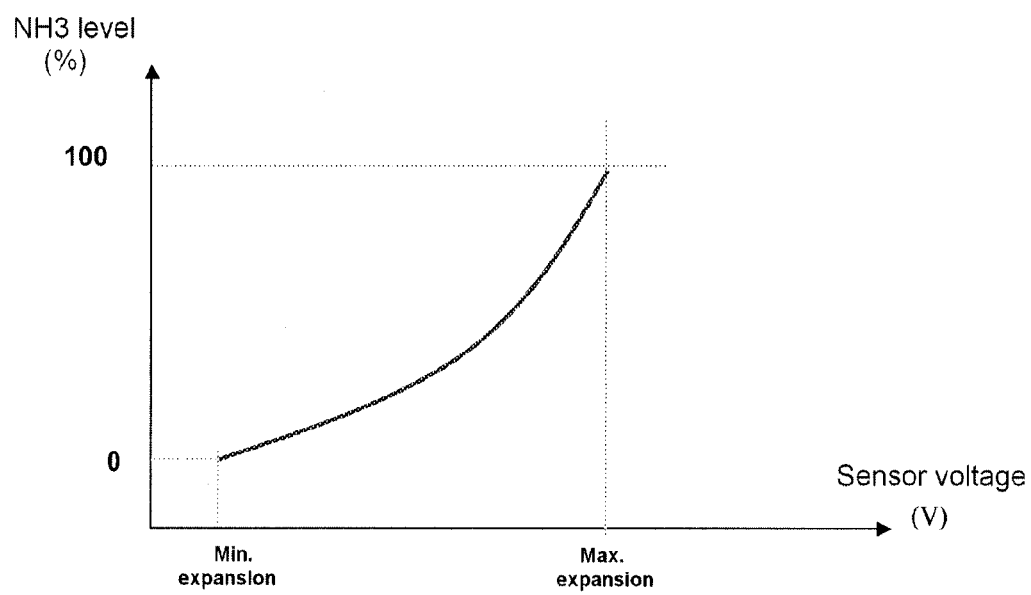
FIG. 5 illustrates the change in stress measured by the means of measuring mechanical stress as a function of the level of ammonia in the vessel.

For these three embodiments of the invention, the change in mechanical stress caused by expansion of the storage material during a complete desorption cycle can be directly correlated with the ammonia present in the vessel. Thus, it is possible to define by calibration for the vessel considered the level of ammonia remaining by measuring the voltage at the terminals of the piezoelectric material as represented schematically in FIG. 5.

Figure 6:
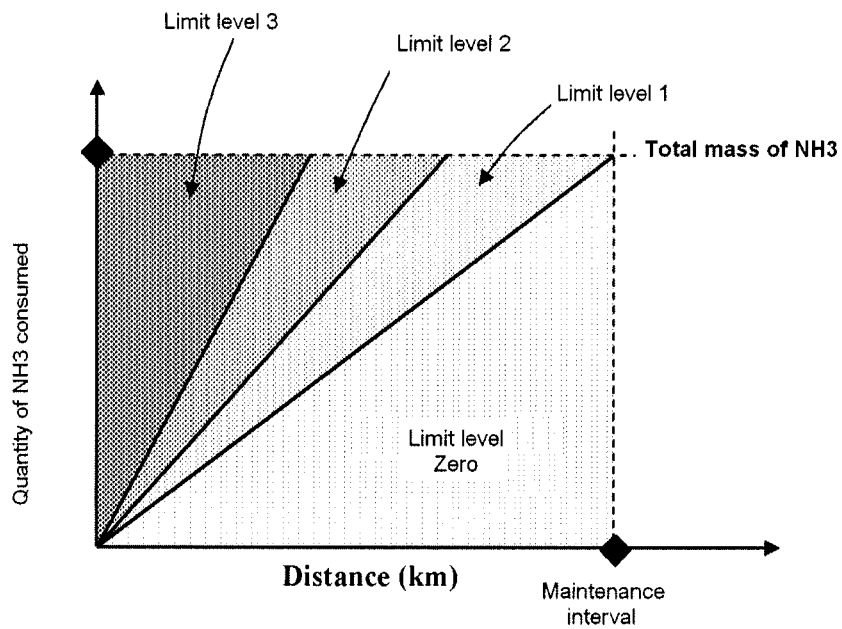
FIG. 6 represents a map for determining the ammonia consumption limit.

Periodic maintenance service, preferentially scheduled with engine maintenance (oil change) or refueling, is carried out to fill the vessel comprising the storage material of the invention with ammonia. The vessel emptied of ammonia can also be replaced with a new vessel whose storage material is saturated with ammonia. The gauging of the remaining ammonia described above associated with acquisition of the maintenance service makes it possible according to the invention to determine by calculation an average consumption of ammonia since the last maintenance service. In the present invention, this measured average consumption is compared with various threshold values with the objective of adapting consumption strategies in order to, if need be, limit this consumption and thus to ensure a sufficient reserve of ammonia to reach the theoretical maintenance step of the vessel. In practice, the quantity of ammonia consumed since the last maintenance service measured via the use of one or more piezoelectric sensors determines a limit level by means of a map as defined in FIG. 6.

Typically, as long as the consumption of ammonia remains below threshold level 1, limit level zero is active (i.e., no correction of the quantity of ammonia injected). If, after a certain distance traveled, the consumption of ammonia comes to exceed the level 1 threshold curve, limit level 1 is activated and the corresponding corrections are then applied.

Figure 7:
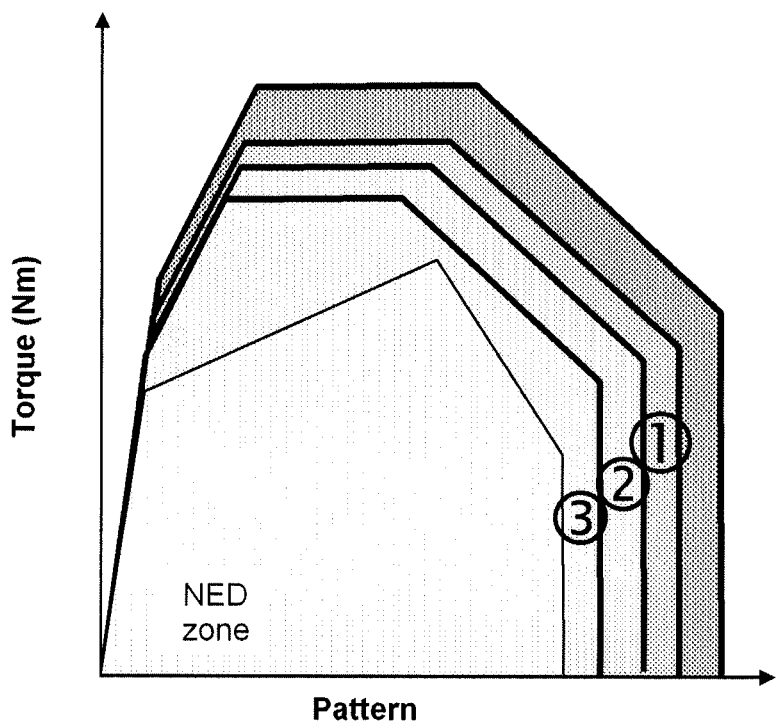
FIG. 7 represents a correction map for the quantity of ammonia to be injected.

For each limit level, a correction is applied to the quantity of ammonia to be injected calculated for the NOx conversion requirements of the SCR post-treatment device. This correction coefficient, applied in the form of a multiplicative coefficient of less than 1, is determined for each limit level by means of a pattern/load map as represented in FIG. 7, where the New European Driving Cycle (NEDC) zone is the zone covered during a homologation cycle. According to this figure, ammonia consumption is progressively limited by three correction coefficients, once the engine is operating in zone 1, then in zone 2, and finally in zone 3, respectively. The parameters ambient temperature, altitude and engine water temperature can also be taken into account to determine the value of the correction coefficient.

Figure 8:
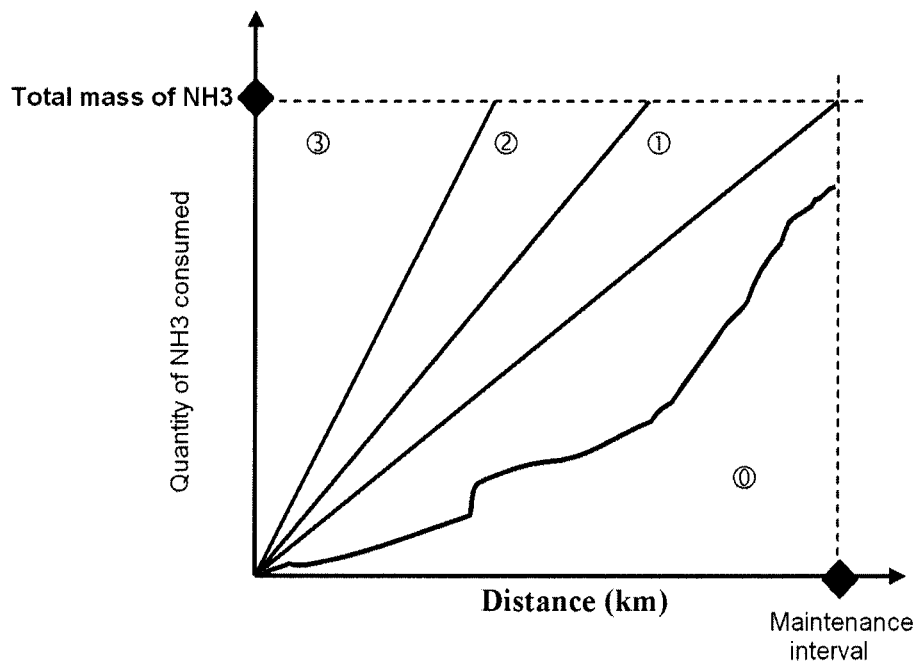
FIG. 8 represents change in the quantity of ammonia consumed as a function of distance traveled by the motor vehicle under so-called average driving conditions.
Figure 9:
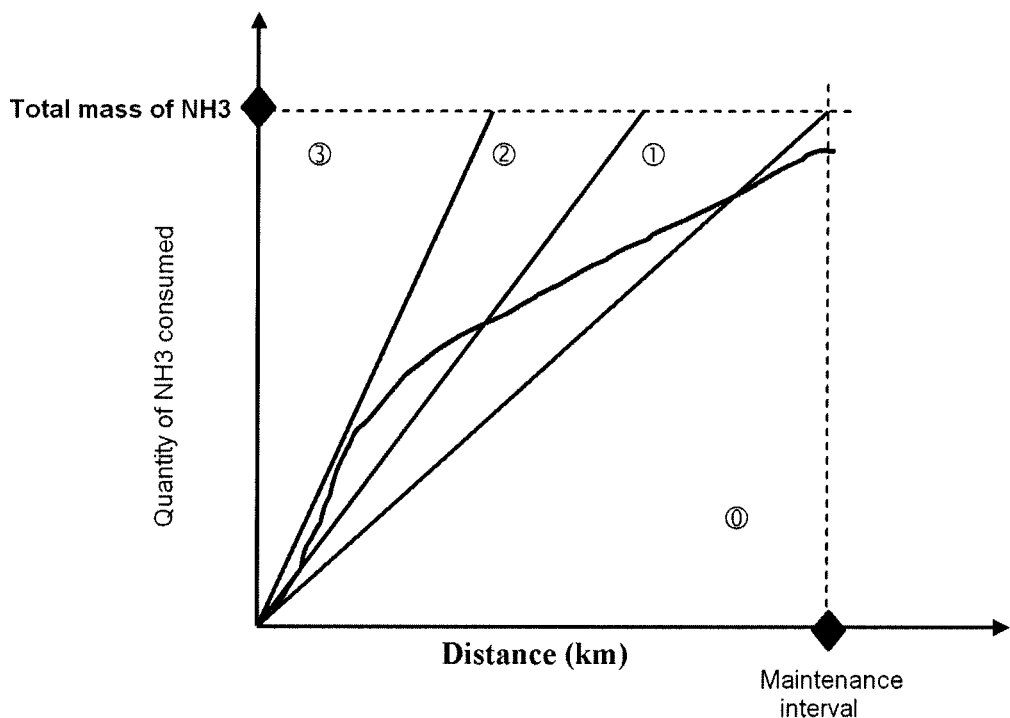
FIG. 9 represents change in the quantity of ammonia consumed, which was limited under so-called severe driving conditions.

By establishing these successive limit levels it becomes possible to control the consumption of ammonia in a manner adapted to each customer's driving conditions. Given that most customers experience average driving conditions, the injection of ammonia is not corrected and the maximum efficiency of the system is obtained (FIG. 8). For the 10% of customers with severe driving conditions, the uncorrected injection of ammonia would result in the consumption of the totality of the ammonia stored in the vessel before the oil-change interval. Establishing limit levels makes it possible to progressively limit the consumption of ammonia, at the cost of a reduction of the efficiency of the system, and thus to ensure the operation of the system until the oil-change interval (FIG. 9).

It goes without saying that the invention is not limited to the embodiments described above as examples but that, on the contrary, it embraces all variants of embodiments. For example, the measuring device can also be used to estimate the quantity of hydride of a fuel cell of a hydrogen storage system.

The invention claimed is:

1. A device for measuring a quantity of a reducing agent, contained in a vessel containing a storage material in which the reducing agent is stored, the volume of the storage material varying depending on the quantity of reducing agent that it contains, the measuring device comprising means associated with the vessel, said means for measuring the quantity of reducing agent stored in the storage material depending on the volume of the latter, by measuring mechanical stress generated by expansion of the storage material, and converting the stress measurement into a quantity of reducing agent stored in the storage material.

2. The measuring device of claim 1, wherein said means for measuring mechanical stress generated by expansion of the storage material comprise at least a piezoelectric sensor.

3. The measuring device of claim 2, wherein said means further comprise at least a mobile wall in contact with the storage material, said piezoelectric sensor being arranged to measure mechanical stress related to movement of the mobile wall.

4. The measuring device of claim 1, wherein said means comprise two piezoelectric sensors and two mobile walls, each piezoelectric sensor being associated with a respective mobile wall so as to measure mechanical stress related to movement thereof.

5. The measuring device of claim 3, wherein the at least one mobile wall is permeable to the reducing agent.

6. The measuring device of claim 5, wherein the at least one mobile wall is positioned perpendicular to a longitudinal axis of the vessel.

7. The measuring device of claim 1, wherein said means are arranged around the lateral surface of the storage material.

8. A method for controlling the injection of a reducing agent into the exhaust gases of a motor vehicle, comprising at least the following steps:
measuring the quantity of reducing agent in a vessel feeding the engine with the measuring device of claim 1,
determining the average consumption of reducing agent since the last vessel maintenance service,
comparing said average consumption with at least one threshold value so as to, if need be, limit said consumption so as to have a sufficient quantity of reducing agent to reach the theoretical step of the next vessel maintenance service.

9. The method of claim 8, wherein consumption of the reducing agent is limited according to:
the engine speed, or engine load, or engine water temperature, or the distance traveled by the motor vehicle since the last vessel maintenance service, or
an external parameter, in particular ambient temperature or altitude, or a combination thereof.

10. The measuring device of claim 1, wherein the reducing agent is $NH_3$.

11. The measuring device of claim 4, wherein the at least one mobile wall is permeable to the reducing agent.

12. The measuring device of claim 4, wherein the at least one mobile wall is positioned perpendicular to a longitudinal axis of the vessel.

13. The measuring device of claim 1, wherein the storage material comprises a material having a crystal lattice that expands in response to storage of the reducing agent.

14. A device for measuring a quantity of a reducing agent, contained in a vessel containing a storage material in which the reducing agent is stored, the volume of the storage material varying depending on the quantity of reducing agent that it contains, the measuring device comprising at least one sensor associated with the vessel, said at least one sensor configured to measure the quantity of reducing agent stored in the storage material depending on the volume of the latter, said at least one sensor being arranged on the one hand for measuring mechanical stress generated by expansion of the storage material, wherein the stress measurement is correlated into a quantity of reducing agent stored in the storage material.

15. The measuring device of claim 14, wherein said at least one sensor for measuring mechanical stress generated by expansion of the storage material comprises at least one piezoelectric sensor.

16. The measuring device of claim 15, further comprising at least one mobile wall in contact with the storage material, said piezoelectric sensor being arranged to measure mechanical stress related to movement of the mobile wall.

17. The measuring device of claim 16, wherein the at least one sensor comprises two piezoelectric sensors and the at least one mobile wall comprises two mobile walls, each piezoelectric sensor being associated with a respective mobile wall so as to measure mechanical stress related to movement thereof.

18. The measuring device of claim 16, wherein the at least one mobile wall is permeable to the reducing agent.

19. The measuring device of claim 16, wherein the at least one mobile wall is positioned perpendicular to a longitudinal axis of the vessel.

20. The measuring device of claim 14, wherein the at least one sensor is arranged around the lateral surface of the storage material.

21. The measuring device of claim 14, wherein the storage material comprises a material having a crystal lattice that expands in response to storage of the reducing agent.

22. A method for controlling the injection of a reducing agent into the exhaust gases of a motor vehicle, comprising:
measuring the quantity of reducing agent in a vessel feeding the engine with the measuring device of claim 13,
determining the average consumption of reducing agent since the last vessel maintenance service,
comparing said average consumption with at least one threshold value so as to, if need be, limit said consumption so as to have a sufficient quantity of reducing agent to reach a theoretical step of the next vessel maintenance service.

* * * * *

UNITED STATES PATENT AND TRADEMARK OFFICE
CERTIFICATE OF CORRECTION

PATENT NO. : 9,243,945 B2
APPLICATION NO. : 14/117360
DATED : January 26, 2016
INVENTOR(S) : Arnaud Audouin Page 1 of 1

It is certified that error appears in the above-identified patent and that said Letters Patent is hereby corrected as shown below:

In the Claims

In Column 5, Claim 4, line 24, please delete "claim 1" and insert -- claim 3 --

In Column 5, Claim 6, line 31, please delete "claim 5" and insert -- claim 3 --

Signed and Sealed this
Twenty-third Day of August, 2016

Michelle K. Lee
*Director of the United States Patent and Trademark Office*